United States Patent [19]
Desvignes et al.

[11] Patent Number: 5,931,849
[45] Date of Patent: Aug. 3, 1999

[54] MODULAR SURGERY DEVICE FOR ENDOSCOPIC SURGERY AND STANDARD SURGERY

[75] Inventors: Gérard Desvignes, Montargis; Bernard Posselier, Ferriers; Jacques Rentler, Montargis, all of France

[73] Assignee: Visco, France

[21] Appl. No.: 08/906,394

[22] Filed: Aug. 5, 1997

[30] Foreign Application Priority Data

May 6, 1997 [FR] France ................................. 97 05581

[51] Int. Cl.[6] .................................................. A61B 17/32
[52] U.S. Cl. ..................... 606/167; 606/170; 606/174; 606/205; 606/206; 606/207; 606/208
[58] Field of Search .................................. 606/167, 205, 606/206, 207, 208, 170, 174

[56] References Cited

U.S. PATENT DOCUMENTS

| | | | |
|---|---|---|---|
| 5,562,655 | 10/1996 | Mittelstadt et al. | 606/205 |
| 5,562,694 | 10/1996 | Sauer et al. | 606/205 |
| 5,607,450 | 3/1997 | Zvenyatsky et al. | 606/205 |
| 5,618,257 | 4/1997 | Kulisz et al. | 600/29 |
| 5,782,859 | 7/1998 | Nicholas et al. | 600/205 |

FOREIGN PATENT DOCUMENTS

| | | |
|---|---|---|
| 0555103 | 8/1993 | European Pat. Off. . |
| 0706781 | 4/1996 | European Pat. Off. . |
| 4332497 | 3/1995 | Germany . |
| 4406880 | 8/1995 | Germany . |

*Primary Examiner*—Michael Buiz
*Assistant Examiner*—(Jackie) Tan-uyen T. Ho
*Attorney, Agent, or Firm*—Vorys Sater Seymour & Pease LLP

[57] ABSTRACT

Modular surgical device for endoscopic surgery and standard surgery, wherein it comprises a prehension means equipped with a trigger which, using a control rod, controls the movement of a tool located inside at least one mobile guide tube which rotates with respect to the said prehension means, which is fitted with, on the one hand, a locking system for the amplitude of movement of the tool and, on the other hand, a locking and ejection system for the tool.

26 Claims, 1 Drawing Sheet

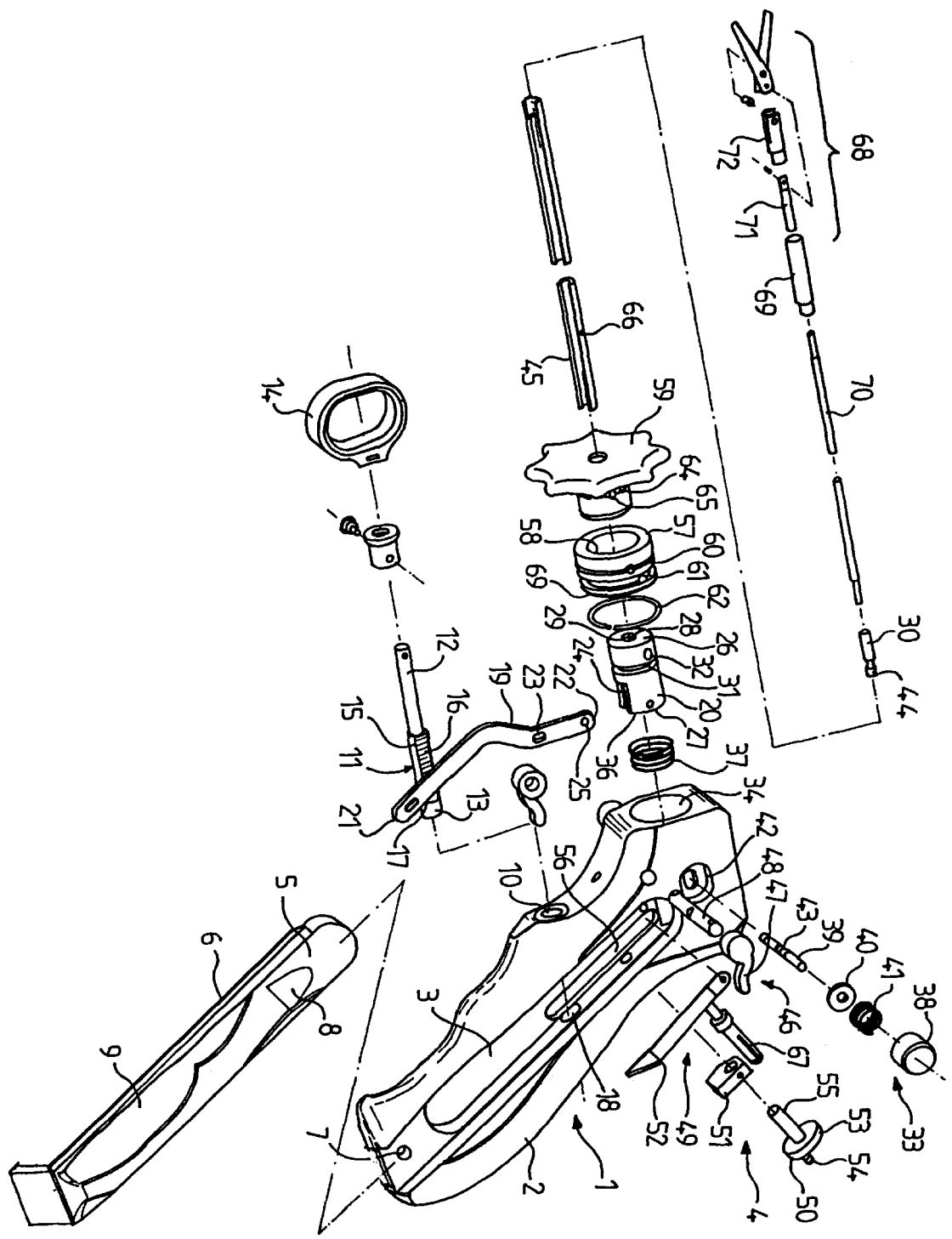

MODULAR SURGERY DEVICE FOR ENDOSCOPIC SURGERY AND STANDARD SURGERY

The present invention relates to a surgical device for endoscopic and standard surgery, in particular in the visceral, thoracic and gynaecological fields.

It relates more particularly to an instrument for prehension by a surgeon's hand which achieves all of the following objectives:

improved safety for the patient, total security for the surgeon, exceptional operating comfort improving the precision of the practitioner's movements, almost immediate interchangability of tools during the operation, extremely easy dismantling and maintenance for sterilisation.

Known instruments of the prior art currently used for endoscopic surgical operations originated in the gynaecological field.

The majority of these instruments were developed from pairs of scissors from which was retained the portion of the handles below the escutcheon, on which the pivot is placed and which allows the practitioner to pass his fingers inside the rings, the other portion comprising the cutting blades having been replaced by a tubular body in which extension rods are connected to one end of the first part, the other end being connected to tools.

Generally, these tools by their very design do not offer optimum ergonomy; handling by use of the fingers passing through the rings can only be carried out correctly if the handles are located in the axis of the wrist. This handling method thus limits the degrees of freedom the practitioner can impart to the tool. Thus, when handled on a horizontal plane, excessive torsion is produced in the wrist joint, which is tiring and renders the surgical operation difficult, with all the negative consequences on precision and rapidity of the movement to be carried out.

Moreover, the active part of these surgical instruments generally comprises connecting rods which activate the forceps or the cutting devices under the effect of the extension rods.

The kinematics of the movement of these connecting rods follow a trajectory which passes the outer clearance of the tool's body, which may provoke unwanted pinching or burning linked to power leaks on healthy areas.

The electrical insulation of these instruments is obtained by applying a heat-shrinkable sheath to the outer body of the tool. This plastic coating tends to become worn over time by the repeated action of passing through an autoclave in order to sterilise the instrument. These localised insulation faults can provoke a risk of burns in unwanted areas, resulting in possible coagulations of healthy tissues.

This electrical insulation problem also applies to areas of prehension by the user's hand. In fact, it is known from experience that a protective glove becomes porous after 30 minutes or risks being damaged by untimely friction linked to delicate handling, which can thus leave areas unprotected. The surgeon is therefore sometimes subjected to electrical shocks which can disturb his comfort and lead to uncontrolled movements.

Furthermore, the range of tools available on this type of mounting is limited, owing to the size of the rod assembly and, in the case of forceps, they generally open asymmetrically as only one arm is movable, while the other remains fixed.

Known tools of the prior art, if not disposable, are re-usable and must therefore be subjected to a sterilisation and decontamination process between operations.

It is therefore necessary to dismantle these instruments for the decontaminant liquid to reach all the surfaces. Now, known tools of the prior art can practically not be dismantled, the majority of the parts being crimped.

Furthermore, as the tools connected to these instruments cannot be dismantled, they cannot be interchanged during the operation, which obliges the practitioner to completely remove the instrument and its specific tool from the trocar, to replace the instrument with one that is suited to the circumstances, which therefore necessitates a large stock, and additional handlings and costs.

The present invention therefore aims to overcome these drawbacks by proposing a completely modular surgical instrument, which offers perfect electrical insulation, which allows easy movements in all directions without tiring the user's hand, which allows the tool to be interchanged rapidly, for improved precision of movements, to ensure comfort and safety, both for the practitioner and for the patient.

To this end, the modular surgery device for endoscopic surgery and standard surgery is characterised in that it comprises a prehension means equipped with a trigger which, using a control rod, controls the movement of a tool located inside at least one mobile guide tube which rotates with respect to the said prehension means, which is fitted with, on the one hand, a locking system for the tool's amplitude of movement and, on the other hand, a locking and ejection system for the tool.

Other characteristics and advantages of the present invention will become apparent from the description below, with reference to the annexed drawings which illustrate an example of its implementation without any limitative nature.

The single figure is a perspective and exploded view of the assembly of parts mounted on the device which is a subject of the invention.

According to a preferred implementation of the surgical device for endoscopic surgery and standard surgery which is a subject of the invention, this comprises prehension means 1 for the surgeon implemented in particular in the form of a handle 2 the principal curvature of which resembles the butt of a revolver. This handle is obtained thanks to a plurality of machinings or by moulding in a composite material of plastic type, offering self-lubricant qualities in particular such as "TECHTRON HPV". It also presents a voluminal portion which perfectly moulds the palm of the surgeon's hand and specific locations for placing fingers and more specifically imprints at the top for thumbs in order to stabilise the handle whatever the supination and/or pronation movements made by a man skilled in the art.

According to another characteristic of the prehension means, their geometry allows their ergonomic use equally with the left hand or the right hand.

The handle 2 comprises a hollow central area which extends approximately along the longitudinal axis of the handle 2 and which is intended to receive the whole mechanical system.

The mechanical system 4 is protected from external stresses by a stopper strip 5, also made of "TECHTRON HPV", which slides in a direction parallel to the main axis of the handle 2 via guide means 6 shaped as slide rails equipped laterally with dovetails, between a locked position and a totally ejected position.

The stopper strip 5 is held in position and locked to the handle 2 via a closing means made in particular of a ball catch 7.

Furthermore, this stopper strip 5 has external profiles 9 allowing prehension of the handle in the palm of the surgeon's hand and also a notch 8 to facilitate its ejection.

This handle 2 also has an opening 10 located in an approximately perpendicular direction to the hollow central area 3 and half-way up the handle 2, this opening 10 allows a control rod 11 comprising two cylindrical parts 12,13, one 12 being connected to a trigger 14, the other 13 being equipped on one face with a flat surface 15 equipped with fine teeth 16 and on the other face with a locating groove 17. This control rod 11 is made of a stainless steel and in order to improve its mechanical characteristics, it is subjected to a certain number of operations (in particular thermal, quenching, electrolytic polishing, special hardness-enhancing coating, and anti-corrosion treatments, etc.). The control rod 11 is guided through the opening 10 of the handle 2, at the front using a bearing also made of "TECHTRON HPV", at the rear using a high-precision bore 18. The front part of the control rod 11 is connected to an approximately oblong-shaped trigger 14, the bore of which is tulip-shaped on each side.

Moreover, this trigger 14 rotates around the control rod 11 is made of a stainless steel and presents an angular displacement which can reach 30° to the right and to the left in relation to the vertical axis of the handle 2, thus allowing easy movement by the index finger or the middle finger of the left hand or the right hand.

The control rod 11 inside the hollow area 3 of the handle 2 cooperates with a control lever 19 also made of stainless steel. This control lever 19 transmits the translational movement originating from the trigger 14 to a control piston 20, the role of which will be explained below, the movement being transmitted at a reduction ratio of approximately 3.5. This control lever 19, very approximately S-shaped, is connected by one 21 of its extremities 21,22 to the control rod 11 via a crimped finger 23 and by the other 22 of its extremities 21,22 to the control piston 20 via a notch 24 provided in it and to a pin 25 for axial immobilisation.

The control piston 20, in particular in stainless steel and of an approximately cylindrical shape, includes at one of its extremities 26, 27, at its front part a bore 28 fitted with an entry cone 29 allowing the passage of the joining piece of the tool 30, at its middle part a circular groove 31.

The front part of the piston 20 also comprises a radial bore 32 which opens into the axial bore 28 and the dimensions of which are compatible with the introduction of the locking and instant ejection system 33 of the joining piece of the tool 30.

The control piston slides in a high-precision bore 34 located in the upper and front part of the handle 2, and in this bore 34 is placed at least one joint 35 (not illustrated), made in particular of "VITON" in order to prevent $CO_2$ or smoke from passing up into the lower part of the handle 2.

The rear part of the piston 20 includes a drain or notch 24 made in a longitudinal direction for the upper part of the control lever 19 to pass through.

This drain 24 also allows decontamination products to drain away easily, as it opens into the central bore 28.

Moreover, the front wall 36 of the rear part of the control piston 20 forms a bearing surface for the spring 37 in stainless steel which mechanically assists the opening of the tool by the operator, producing a 1/1 ratio between the force applied to the trigger 14 and the force transmitted to the head of the tool, and allowing passage of the required high-frequency electric current to the scalpel.

The prehension means 1 according to the invention also has a system for locking and instantly ejecting 33 the whole tool 68 alone, or together with its guide tube 45.

This system 33 includes in particular two knurled push buttons 38, a locking rod 39, a thrust collar 40 and a spring 41.

The push buttons 38 are made of the same material as that constituting the body of the handle 2 or of the stopper strip 5 to guarantee electrical insulation. They are housed in two oblong machinings produced on either side of the lateral faces, in the upper part of the handle 2. The push buttons 38 are connected by a locking rod 39 which includes approximately in its centre a drain 43 intended to cooperate with a conical drain 44 located at the extremity of the joining piece of the tool 30. Locking is achieved by fixing the joining piece of the tool 30 to the control piston 20 via the locking rod 39.

This rod 39, under the action of the user's finger on one of the push buttons 38, moves into the radial bore of the piston and releases the joining piece 30.

An elastic device, in particular a spring 41, located between one of the push buttons 38 and a thrust collar 40 lying against one of the faces of the oblong machinings 42, ensures that the push button 38 returns to its original position.

All the parts comprising the system for locking and instantly ejecting 33 the joining piece of the tool 30 are fully dismantlable in order to facilitate decontamination and sterilisation.

This locking and ejection system 33 either operates only on the joining piece of the tool 30 or on the joining piece of the tool 30 which is connected to the guide tube 45 the role of which will be explained below.

The prehension means 1 according to the invention also includes a system 46 allowing gases and smoke to be extracted. Preferably, one of two levers 47 placed to the left and the right of the handle 2 near the locking and ejection system 33 actions an opening valve 48 allowing the extraction of excess pressure levels of $CO_2$ or smoke generated by the use of an electric scalpel. It should be recalled that a gas, in particular $CO_2$, is blown into the abdominal cavity during coelioscopic operations in order to detach the peritoneum from the organs and thus increase the surface area of the operating area.

The valve 48 opens into an open channel cut in the handle 2.

Moreover, given that the endoscopic surgery operation is carried out with a constant gas pressure and that there must be no leaks, it is envisaged to place airtight joints made in particular of "VITON" along the handling rod of the valve 48.

The prehension means 1 according to the invention is also equipped with a rack locking system 49. Overall, it comprises a control lever 50, a cam 51 and a spring blade 52.

The control lever 50 is located behind the handle 2, approximately in the centre and in the middle part, and is controlled equally well by the left thumb or the right thumb given the symmetry of its profile.

The control lever 50 comprises a disk 53 one face of which is equipped with a protruding lug 54 for handling by the thumb and the other face of which is equipped with an axial part 55 connected to the cam 51. This axial part 55 actions the rotating cam 51 to implement the locking via a stainless steel spring blade 52 which, at rest, activates the rack and locks movement.

The cam 51 made in particular of stainless steel comprises two positions:

one, resting against the spring 52, deactivates the locking system;

the other releases the spring 52 and activates the locking system.

The amplitude of the travel, determined by the user according to his action applied to the trigger 14, determines the intensity of the locking.

The spring blade 52 is crimped in a recess 56 of similar geometry located beneath the control rod.

The prehension means 1 also comprises a ball locking system 57 for the guide tubes 45. This system 57 is obtained from an approximately cylindrical part made from stainless steel, comprising a central bore 58 opening each side, allowing a wheel 59 to be fitted.

The external surface of the ball locking system 57 comprises two circular grooves 60, 61, one 60 intended to make the part lighter, the other 61 being provided with a plurality of radial holes 63, preferably six in number, each filled by a ball, held in place by a stainless steel spring-fitted retaining ring (62) These balls act as a bearing cage for the wheel 59 supporting the guide tubes 45. The ball locking system 57 for the guide tubes 45 is mounted on the front wall of the handle 2 and encloses the retaining ring 62.

The last sub-assembly connected to the surgical device 1 which is a subject of the invention is constituted by the guide tubes 45. These tubes 45 made of stainless steel are of different lengths and different diameters and, at one extremity, comprise a wheel 59 presenting a shoulder on which a circular groove 64 is machined which, when coupled with the handle 2, allows the guide tubes 45 to snap into it. A ring of spherical impressions machined into this groove 64 allows, via ball catches, indexation of the tool by a variable step according to the number of balls enclosed in the cages; in this implementation example, indexation is every 60°.

The user controls the rotation of the wheel 59 and of the guide tubes 45 which are fixed to it via notches 65 cut on the periphery of the wheel 59. In order not to risk damaging the protective glove of the user's hand, the notches 65 have rounded edges.

The guide tubes 45 are forced on and crimped in an opening cut in the centre of the said wheel 59.

In order not to interfere with the adjustment of the camera which is used during the surgical operation, and in particular in order to avoid the excessive brightness responsible for the automatic adjustment of the camera's diaphragm and of the light source, which may generate a blank screen on the control monitor for several seconds, the external surfaces of the wheel 59 and of the guide tubes 45 are subjected to surface treatment in particular in the form of chemical coloring in matte black.

Provision is also made for an opening 66 on at least one of the guide tubes 45, crossing the entire wall and used to extract smoke and excess $CO_2$ pressure which escape via the valve 48 located beneath the handle 2, such escape being controlled by the user as described above.

The electricity supply to the prehension means is provided via an electric socket 67, one or two pin, located in the rear portion of the handle 2 and approximately in the upper part. This socket 67 is inclined with respect to the horizontal axis, so that the surgeon's hand is not hindered by the electricity cable coming from the electric scalpel.

This socket 67 is connected to the spring 37 located to the rear of the control piston 20 which transmits current to the joining piece of the tool 30. The electrical insulation of the prehension means 1 is provided by the choice of material constituting it and of the material constituting the other sub-assemblies mounted on the handle. The surgeon thus no longer risks experiencing electric shocks to the hand, even if his glove is pierced or has become porous.

The guide tubes 45 allow surgical tools 68 of varying diameter and length to pass and slide within them.

These tools 68 comprise at least one control rod 70, the external wall of which is coated with an electrical insulation layer, avoiding any unwanted cases of electric arcing, the rod being connected by one of its extremitites to a joining piece 30 which passes through the wheel 59 and the control piston 20, and by the other extremity to an insulating sleeve tube 69 in which the extremity of the control rod 70 slides. This same rod extremity 70 is connected to a connecting rod 71 which cooperates with a cover 72 and the head of the tool 68 itself. This head can be constituted by a pair of scissors, a pair of forceps which may or may not open symmetrically, a clamp forceps, a cutting blade, a one or two pin coagulation tool, etc.

The invention described above offers numerous advantages owing to the ergonomic shape of the handle and the symmetrical installation of the controls for the various features, guaranteeing optimum use, both with the left hand and with the right hand, and whatever the size of the hand.

Also, owing to the type of material constituting all the components mounted on this handle and their surface treatment preventing organic materials from getting caught, maintenance is reduced to its simplest expression. Only a limited number of components, which can all be dismantled, facilitates efficient decontamination and sterilisation.

It remains of course that the present invention is not limited to the implementation examples described and represented above, but it encompasses all variants, in particular both as regards the materials used (plastic, composite, grade of stainless steel, etc.) and as regards thermal treatments, protection treatments, treatments improving the mechanical characteristics of the materials, but also the materials constituting the assembly of parts, in particular the joints, the electrical insulation sheaths, etc.

We claim:

1. A modular surgical device comprising:
   a handle shaped to fit within a hand of an operator and having a rear wall toward the thumb of the hand, a first sidewall toward the palm of the hand, a front wall toward fingers of the hand, and a second sidewall toward fingertips, when the handle is within the hand, the handle also having a top wall, a bottom wall, an enclosed hollow portion therein, and a bore extending from the front wall adjacent to the top wall;
   a piston supported for reciprocative movement in the bore;
   a control rod supported for reciprocative movement through an opening in the front wall of the handle between the bore and the bottom wall, the control rod extending into the hollow portion of the handle;
   a trigger attached to an end of the control rod externally of the handle for moving the control rod;
   a coupling between the control rod and the piston for causing the piston to move in response to movement of the control rod;
   a locking mechanism for releasably locking the control rod at different positions reached by control rod movement; and
   a tool assembly releasably coupleable to the piston.

2. A modular surgical device according to claim 1, wherein the trigger is supported on the control rod for pivotal movement about a longitudinal axis of the control rod to permit the trigger to be tilted leftward and rightward relative to the handle.

3. A modular surgical device according to claim 1, wherein the locking mechanism includes a rack on a portion of the control rod in the hollow portion of the handle, a locking element engageable with the rack in the hollow portion, and a control member having a part coupled to the locking element through a wall of the handle and a manually-engageable part externally of the handle.

4. A modular surgical device according to claim 3, wherein the manually-engageable part is disposed at the rear wall of the handle for engagement by the thumb of the operator's hand.

5. A modular surgical device according to claim 1, wherein one of the sidewalls of the handle has a first portion slidably mounted on a second portion of that sidewall to expose the hollow portion of the handle.

6. A modular surgical device according to claim 5, wherein the first portion is part of the second sidewall of the handle and has depressions for receiving fingertips of the operator's hand.

7. A modular surgical device according to claim 1, wherein the tool assembly includes a guide tube, a control rod supported for reciprocative movement in the guide tube, a tool coupled to one end of the control rod, and a joining piece coupled to an opposite end of the control rod, the joining piece being releasably connected to the piston.

8. A modular surgical device according to claim 7, wherein the handle has a release mechanism supported thereon and operable for releasing the joining piece from the piston.

9. A modular surgical device according to claim 8, wherein the release mechanism includes a manually-operable actuator supported on the handle adjacent to the top wall of the handle.

10. A modular surgical device according to claim 8, wherein the release mechanism includes a pair of spring-biased manually-operable buttons mounted on opposite sides of the handle and coupled to the piston for releasing the joining piece when either button is operated manually.

11. A modular surgical device according to claim 7, further comprising a spring that biases the piston outwardly of the bore.

12. A modular surgical device according to claim 7, wherein the guide tube is attached to a rotational member for rotating the guide tube and the tool about a longitudinal axis of the guide tube.

13. A modular surgical device according to claim 12, wherein the rotational member has an indexing mechanism that provides predetermined releasably set rotational positions.

14. A modular surgical device according to claim 12, wherein the rotational member includes a wheel.

15. A modular surgical device according to claim 1, wherein the device has a system of passages for passing fluid between the tool assembly and an opening on the handle.

16. A modular surgical device according to claim 15, wherein the system includes a passage in the piston.

17. A modular surgical device according to claim 15, wherein the system includes a valve manually operated by an actuator mounted on an upper portion of the handle.

18. A modular surgical device according to claim 1, wherein the device includes an insulated system for conducting electric current to the tool from an electrical connector mounted on the handle.

19. A modular surgical device according to claim 1, wherein the piston has a bore shaped to receive an end of a joining piece of the tool assembly.

20. A modular surgery device comprising a handle shaped to be held by a hand of an operator, a trigger assembly mounted on the handle and disposed for engagement with a finger of the operator's hand to cause the trigger to move on the handle reciprocatively, and a tool assembly mounted on the handle and coupled to the trigger for operation in response to movement of the trigger, wherein the trigger is supported for rotation leftward and rightward with respect to the handle.

21. A modular surgery device comprising a handle shaped to be held by a hand of an operator, a trigger assembly mounted on the handle and including a trigger disposed for engagement with a finger of the operator's hand to cause the trigger assembly to move on the handle reciprocatively, and a tool assembly mounted on the handle and coupled to the trigger assembly for operation in response to movement of the trigger assembly, wherein the handle has front, rear, side, top and bottom walls enclosing a hollow portion therein and the trigger assembly includes a control rod extending into the hollow portion through the front wall of the handle and supported on the handle for longitudinal reciprocative movement, and wherein the device comprises a locking mechanism in the hollow portion for releasably locking the longitudinal position of the control rod, and a manually-operable control member on the handle for releasing the locking mechanism.

22. A device according to claim 21, wherein the control rod is coupled to the tool assembly by a coupling that includes a piston reciprocatively mounted in a bore of the handle and that is releasably coupled to the tool assembly.

23. A device according to claim 21, wherein the tool assembly includes a guide tube with a control rod reciprocatively supported therein for operating a tool, the tool assembly being coupled to the piston in a manner that provides for rotation of the tool about a longitudinal axis of the guide tube.

24. A modular surgery device comprising a handle shaped to be held by a hand of an operator, a trigger mounted on the handle and disposed for operation by the operator's hand to move the trigger on the handle reciprocatively, and a tool assembly mounted on the handle and coupled to the trigger for operation in response to movement of the trigger, wherein the device has a system of insulated conductors for conducting electric current to a tool of the tool assembly from an electrical connector mounted on the handle at a position on the handle and with a disposition so that the hand of the operator is not hindered by an electrical cable extending from the connector.

25. A modular surgery device comprising a handle shaped to be held by a hand of an operator, a trigger mounted on the handle and disposed for operation by the operator's hand to move the trigger on the handle, and a tool assembly mounted on the handle and coupled to the trigger for operation in response to movement of the trigger, wherein the device has a system of passages for passing fluid between the tool assembly and an opening on the handle.

26. A device according to claim 25, wherein said system of passages includes a manually-operable valve on the handle for opening a fluid path through said passages.

* * * * *